United States Patent [19]

Durbin

[11] 4,173,145
[45] Nov. 6, 1979

[54] SOLVENT WASH SYSTEM FOR A CHROMATOGRAPHIC ANALYZER

[75] Inventor: Damien E. Durbin, Martin City, Tex.

[73] Assignee: Honeywell Inc., Minneapolis, Minn.

[21] Appl. No.: 858,786

[22] Filed: Dec. 8, 1977

[51] Int. Cl.² .......................................... G01N 31/08
[52] U.S. Cl. ................................. 73/422 GC; 73/23.1
[58] Field of Search ......................... 73/422 GC, 23.1

[56] References Cited

U.S. PATENT DOCUMENTS

| | | | |
|---|---|---|---|
| 3,156,548 | 11/1964 | Perry | 73/23.1 X |
| 3,245,269 | 4/1966 | Ivie | 73/23.1 X |
| 3,253,455 | 5/1966 | Ferrin | 73/23.1 |
| 3,372,573 | 3/1968 | Sanford et al. | 73/23.1 |
| 3,451,255 | 6/1969 | Neville et al. | 73/23.1 |
| 3,489,011 | 1/1970 | Firman et al. | 73/422 GC |
| 3,545,279 | 12/1970 | Jentzsch et al. | 73/422 GC |
| 3,607,075 | 9/1971 | Wolf | 73/23.1 X |
| 3,881,892 | 5/1975 | Gehrke et al. | 55/67 |
| 3,954,617 | 5/1976 | Ishimatsu | 210/198 C |
| 4,006,624 | 2/1977 | Annino et al. | 73/23.1 |
| 4,007,626 | 2/1977 | Roof et al. | 73/23.1 |

Primary Examiner—Daniel M. Yasich
Attorney, Agent, or Firm—Laurence J. Marhoefer; Lockwood D. Burton; Mitchell J. Halista

[57] ABSTRACT

A fluid valving system for a chromatographic analyzer apparatus has an analyzer oven with a sampling valve and fluid sample storage loop therein while switching valves for directing a sample to be analyzed, a carrier gas and a wash solvent through the sample loop and the sampling valve are located externally to the oven. A timer is used to operate the switching valves and the sampling valve in a desired sequence which includes directing the wash solvent through the storage loop and sample lines while maintaining a flow of carrier gas through a chromatographic column connected to the sampling valve.

8 Claims, 4 Drawing Figures

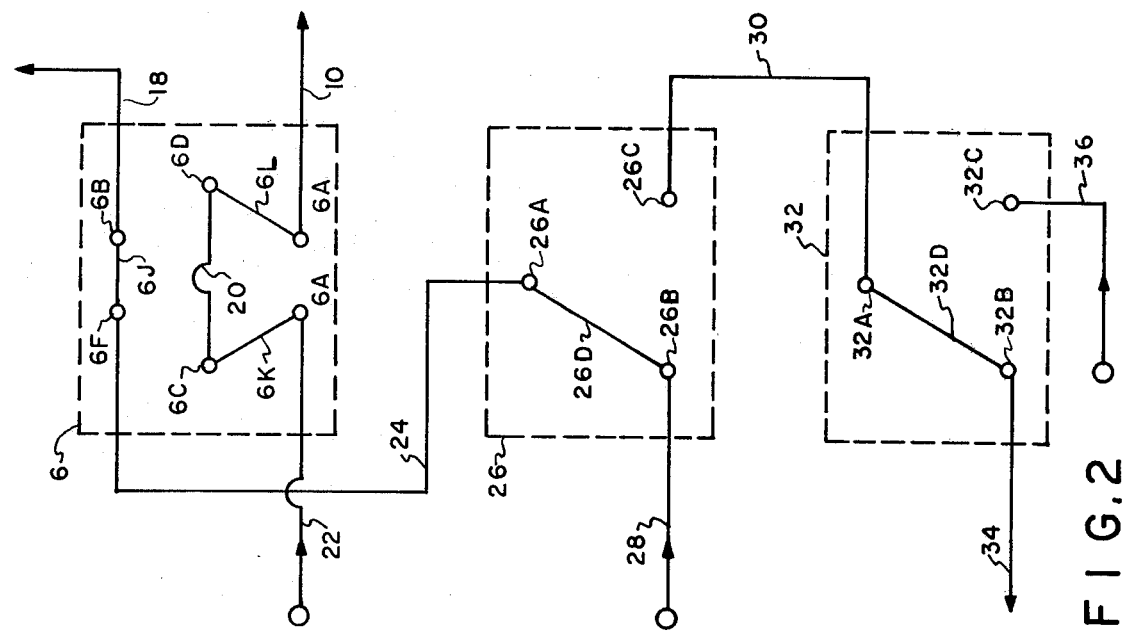
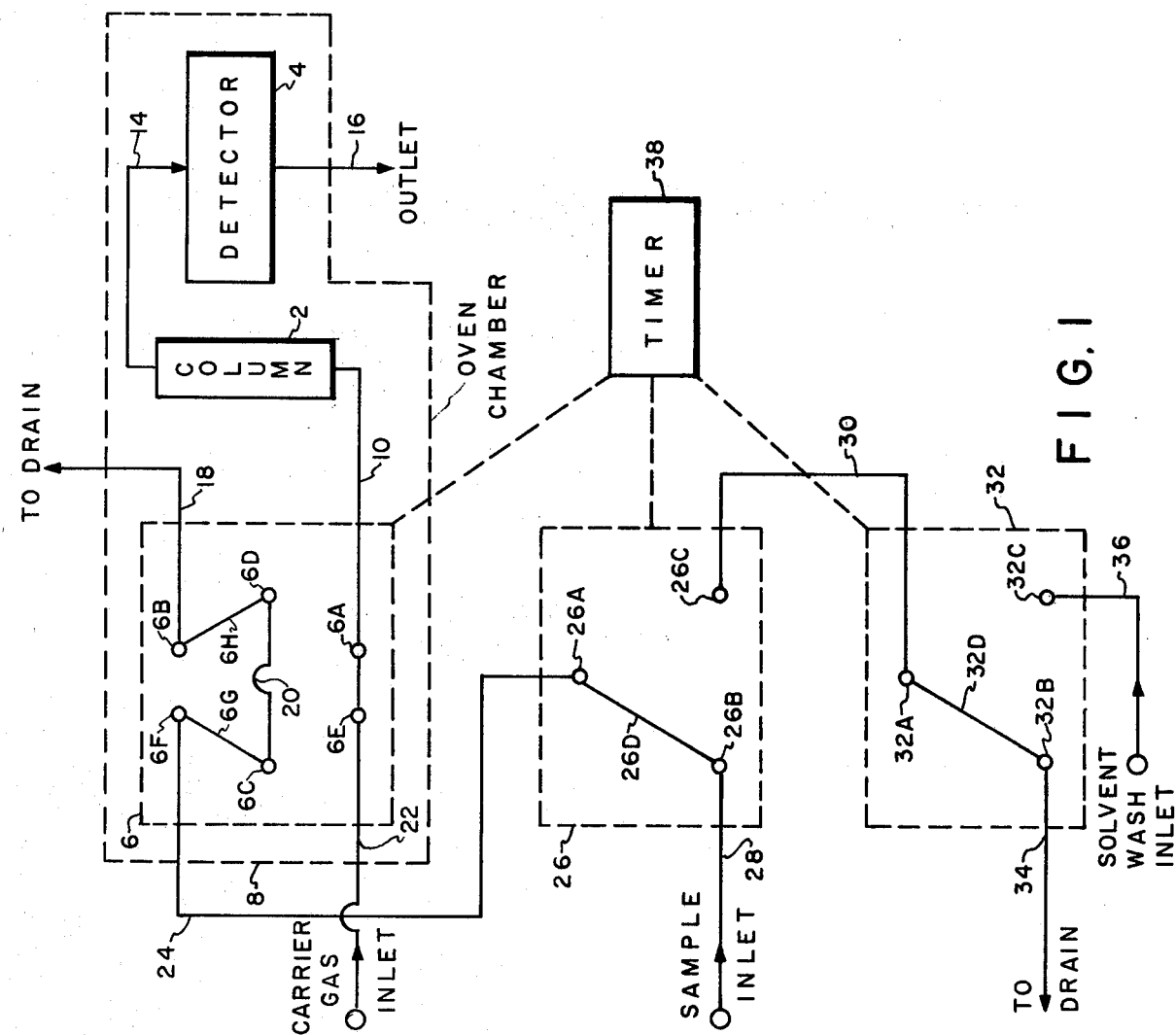

SOLVENT WASH SYSTEM FOR A CHROMATOGRAPHIC ANALYZER

BACKGROUND OF THE INVENTION

1. Field Of The Invention

The present invention relates to chromatographic analyzers. More specifically, the present invention relates to a solvent wash and process stream valving system for a chromatographic analyzer.

2. Description Of The Prior Art

The use of chromatographic analyzers in process control involves the determination of the concentration of constituents in a sample fluid. The sample fluid to be analyzed is introduced into an analyzer column containing a selective constituent partitioning material. A carrier gas is also directed into the column to force the sample material therethrough. In order to provide for liquid samples containing soluble nonvolitile constituents which upon vaporization of liquid sample can become deposited in the sample valve and connecting fluid lines of the chromatographic analyzers, suspended particulates and heat produced polymeric residues which result in plugged lines and valves, the use of a solvent wash technique to clean the valve and the lines using a wash solvent was developed. The solvent wash liquid is passed through the sampling, i.e., valving and fluid conduit zone after the sample to be analyzed and the carrier gas is passed through the sampling zone. A typical prior art solvent apparatus in a chromatographic analyzer is shown in U.S. Pat. No. 3,372,573. However, in such a prior art solvent wash system, the process stream containing the samples to be analyzed continually flows through the sample valve which is located in the heated analyzer oven. The application of heat to that sampled stream often results in a continual deposition of solid material, e.g., polymeric residue inside the sample valve as well as the sample line located inside the oven. Further, the prior art solvent wash systems do not provide for exclusion of solvent leakage into the chromatographic column.

SUMMARY OF THE INVENTION

An object of the present invention is to provide an improved chromatographic analysis system.

Another object of the present invention is to provide an improved chromatographic analyzer having a solvent wash system which obviates the shortcomings of the prior systems.

In accomplishing these and other objects, there has been provided, in accordance with the present invention a chromatographic analyzer system having a solvent wash system with a sampling valve and an analyzer column connected to an output of the sampling valve while respective switching valves are provided for controlling the flow of a sample fluid and carrier fluid to the sample valve and the analyzer column and a solvent wash to the sample valve and the associated fluid conduits. A timer is used to operate the switching valves and the sampling valve in a desired sequence which includes directing the wash solvent through the storage loop and sample lines while maintaining a flow of carrier gas through a chromatographic column connected to the sampling valve.

BRIEF DESCRIPTION OF THE DRAWINGS

A better understanding of the present invention may be had when the following detailed description is read in connection with the accompanying drawings, in which:

FIG. 1 is a schematic illustration of a chromatographic analyzer system having a solvent wash and embodying the present invention and FIGS. 2 to 4 are schematic illustrations of progressive operations of the chromatographic analyzer system shown in FIG. 1.

DESCRIPTION OF THE PREFERRED EMBODIMENT

DETAILED DESCRIPTION

Figure 3:
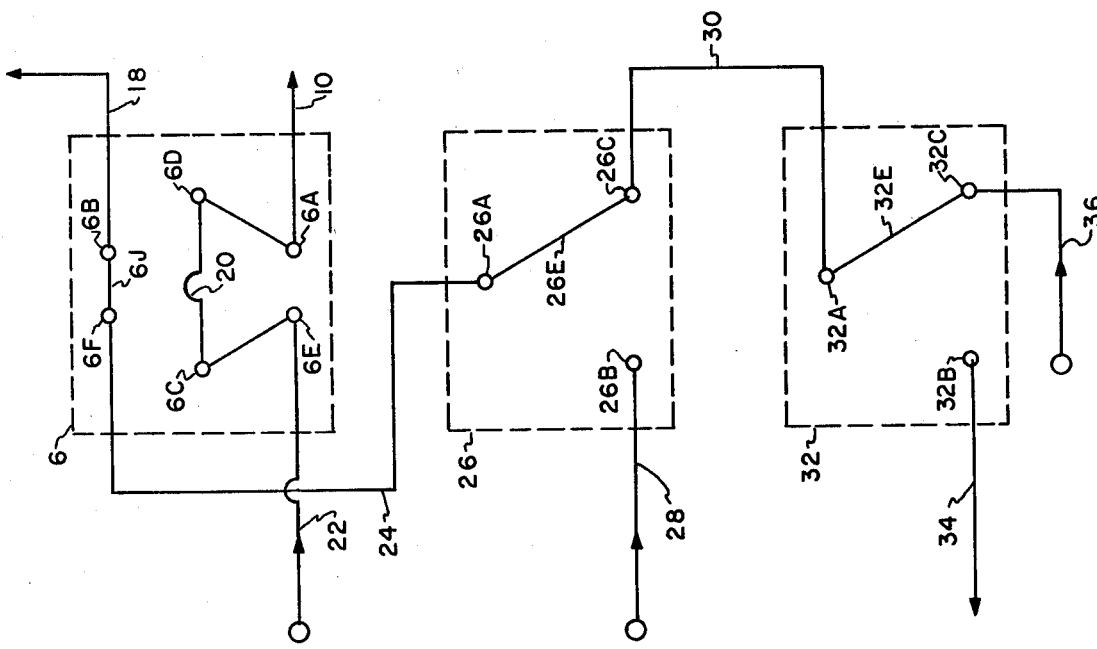

Referring to FIG. 1 in more detail, there is shown a chromatographic analyzer system having a chromatographic column 2, a detector 4 and a sampling valve 6 located within an oven chamber 8 along with interconnecting fluid conduits 10 and 14. A first fluid conduit 10 is arranged to connect an outlet port 6A of the valve 6 to an inlet of the chromatographic column 2 while the second conduit 14 is arranged to connect an outlet from the column 2 to an inlet of the detector 4. An outlet of the detector 4 is connected to an outlet conduit 16 which emerges from the oven 8 to be connected to a fluid outlet (not shown). A second outlet port 6B of the valve 6 is connected to an outlet conduit 18 which is also arranged to emerge from the oven 8 and is connected to a fluid drain (not shown). A sample loop 20 for trapping a sample of the fluid to be analyzed is connected between two ports 6C and 6D of the valve 6 while an inlet port 6E of the valve 6 is connected to a conduit 22 for connection to a source of a suitable carrier gas (not shown), e.g., helium. Finally, an inlet port 6F is connected by a conduit 24 which emerges from the oven 8 and connects the inlet port 6F to an outlet port of a first fluid switching valve 26. Specifically, the conduit 24 is connected to a outlet port 26A of the valve 26.

An inlet port 26B of the valve 26 is connected to a conduit 28 which is arranged to be connected to a sample supply (not shown) for supplying a sample to be analyzed by the chromatographic column 2. A second inlet port 26C of the valve 26 is connected by a conduit 30 to an outlet port 32A of a second fluid switching valve 32. An inlet port 32B of the second switching valve 32 is connected by a conduit 34 to a drain (not shown). A second inlet port 32C of the valve 32 is connected to a source of a wash solvent (not shown) via conduit 36. The wash solvent is a suitable liquid capable of removing deposited materials contained in the conduits and sample loop 20 as hereinafter described. For example, toulene would be a suitable solvent for polymer deposits while water could be used as a solvent for dissolved salt deposits.

The valves 6, 26 and 32 are operated by a timer 38 which may be any suitable apparatus well known in the art for providing control signals in a desired sequence for positioning the valves 6, 26 and 32 to achieve the sequential positions used in the operation of the chromatographic system embodying the present invention. These positions are illustrated in FIGS. 1 through 4. For example, the timer 38 may be an electro-mechanical timer using cam operated switches or an electronic timer generating clock signals which are used to energize the vales 6, 26 and 32. The use of such multi-port valves capable of interconnecting predetermined inlet and outlet ports and timers for sequencing the valves is well-known in the art and a further detailed discussion thereof is believed to be unnecessary in the description of the embodiment of the present invention.

MODE OF OPERATION

The sequential positions of the valves 6, 26 and 32 are shown in the FIGS. 1 through 4 wherein each of the figures illustrates a position of the valves 6, 26 and 32 to achieve a desired function within the chromatographic system embodying the present invention. Specifically, in FIG. 1, there is shown a first position of the valves 6, 26 and 32 which affords an initial sampling system for admitting a sample to be analyzed to the sample loop 20. Thus, the sample fluid is admitted into conduit 28 and is passed to the inlet port 26B of the first valve 26. In the illustrated position of valve 26 in FIG. 1, an internal valve conduit 26D is arranged to connect the inlet port 26B to the outlet port 26A. After leaving the outlet port 26A the sample fluid is conducted via conduit 24 to the inlet port 6F of the valve 6. An internal conduit 6G of the valve 6 in the position of the valve 6 illustrated in FIG. 1 is arranged to connect the inlet port 6F to the sample loop port 6C. Thus, the sample fluid is passed via the internal conduit 6G to the sample loop 20 via the port 6C. After leaving the sample loop 20, the sample fluid is passed via the port 6D of the valve 6 to an internal conduit 6H connected to the outlet port 6B. Finally, the fluid leaves the outlet 6B to an outlet conduit 18 which passes the sample fluid to the drain. Accordingly, at this time the sample fluid is flowing through the sample loop 20 within the oven 8. The position of the second valve 32 in the illustration of FIG. 1 is arranged to provide an internal conduit 32D between the outlet port 32B and the inlet port 32A. Since the inlet port 32B is connected to the drain via conduit 34, this position of the second valve 32 does not affect the sample flow described above.

A first sequential operation of the timer 38 is arranged to produce the positions of the internal conduits of the valves 6, 26 and 32 shown in FIG. 2. For purposes of clarifying the illustration of FIGS. 2, 3 and 4 relating to the positions of the valves 6, 26 and 32 the extraneous elements including the oven 8, the column 2, the detector 4 have been omitted.

As shown in FIG. 2, the second valve 32 is retained in the position shown in FIG. 1. Similarly, the second valve 26 is retained in the same position as that illustrated in FIG. 1. However, the sampling valve 6 is switched to a second position wherein the sample loop 20 is disconnected from the ports 6B and 6F by the removal of the internal conduits 6G and 6H. However, an internal conduit 6J is now provided between outlet port 6B and outlet port 6F whereby the sample fluid being supplied by the first valve 26 in conduit 24 is passed via the inlet port 6F, the internal conduit 6J and the outlet port 6B to the conduit 18 which allows the sample fluid to flow to the drain. Concurrently, the sample loop 20 is connected across the ports 6A and 6E. Specifically, an internal conduit 6K is provided between the inlet port 6E and the port 6C which is connected to one end of the loop 20 while an internal conduit 6L is concurrently provided between the outlet port 6A and the port 6D which is connected to the other end of the loop 20.

In this position of the sampling valve 6, the carrier gas supplied via conduit 22 is passed by the internal conduit 6K from the inlet port 6E to one end of the sample loop 20 at port 6C. The carrier gas is effective to force the fluid sample to be analyzed in the sample loop 20 out of port 6D and, via the internal conduit 6L and the outlet port 6A, into the conduit 10. The sample is, accordingly, forced into one end of the chromatographic column 2. The column 2, as is well known in the art, is filled with a packing material which selectively retards the passage therethrough of constituents of a fluid sample to be analyzed. This results in the various constituents of the fluid mixture to be analyzed flowing through the column 2 at different rates of speed depending on their respective affinity for the packing material of the column. The column 2 accordingly, produces at its outlet an effluent which has the individual constituents of the fluid mixture distributed at spaced time intervals.

These constituents are passed by the conduit 14 to the detector 4. A conventional method of detecting the presence and concentration of these constituents is to employ a thermal conductivity detector which compares the thermal conductivity of the column effluent with the thermal conductivity of the carrier gas or some other reference standard. Thus, the detector 4 can include a temperature-sensitive resistance element placed in the path of fluid flow from the column 2. Concurrently, a reference element (not shown) can be placed in a pure carrier gas flow. Resistance differences between the resistance elements can be measured by any suitable well-known techniques such as an electrical bridge circuit to produce an output signal indicative of the presence and concentration of the various constituents of the fluid to be analyzed. The detector accordingly provides signals representative of a difference between the thermal conductivity produced by the column effluent and that produced by the carrier gas. The analysis of the fluid is completed when the carrier gas alone reaches the detector to provide an output signal from the measuring resistance element equal to that of the reference signal from the reference resistance element.

The timer 38 is operated subsequently either during the analysis of the fluid sample by the detector 4 or after the passage of a period of time suitable for the completion of an analysis by the detector 4 to produce the valve positions illustrated in FIG. 3. In the valve positions of FIG. 3, the first and second valves 26 and 32 are both operated to a second position. In this second position, the second valve 32 is arranged to provide an internal conduit 32E for connecting the inlet port 32C with the outlet port 32A. In this position of the valve 32, the wash solvent is passed from the conduit 36 via the inlet port 32C, the internal conduit 32E and the outlet port 32A to the conduit 30. Since the first valve 26 has also been operated to a second position, it is effective to provide an internal conduit 26E to connect the inlet port 26C with the outlet port 26A. Accordingly, the wash solvent in the conduit 30 is further passed via the inlet port 26C, the internal conduit 26E and the outlet port 26A to the conduit 24. In other words, the second position of the first valve 26 is effective to disconnect the source of the sample to be analyzed from the conduit 24 and to replace it with a connection to the source of the wash solvent. Accordingly, the wash solvent is passed by conduit 24 to the inlet port 6F of the sample valve 6 where it is applied to the internal conduit 6J, the outlet port 6B and the drain conduit 18. Consequently, the solvent wash is effective to clean the outlet port 26A of the valve 26, the conduit 24, the inlet port 6F, the internal conduit 6J, the outlet port 6B, and the drain conduit 18.

Figure 4:
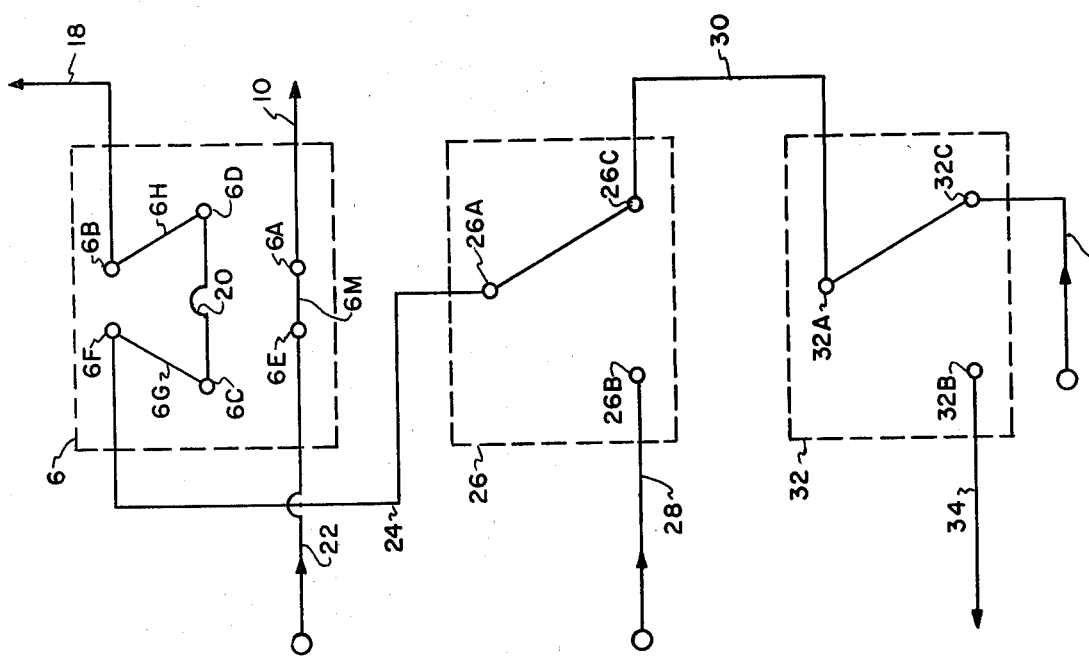

After a suitable length of time to allow the analysis of the fluids sample to be completed by the detector 4, the timer is arranged to operate the valves 6, 26 and 32 to the fourth position shown in FIG. 4. In this position, the first and second valves 26 and 32 are retained in the second state shown in FIG. 3 and previously described. However, the sampling valve 6 is operated to a third position wherein the inlet port 6E is connected by an internal conduit 6M to the outlet port 6A. In this state of the sampling valve 6, the carrier gas in conduit 22 is passed via conduit 22, the inlet port 6E, the internal conduit 6M and the outlet port 6A to the conduit 10 which is connected to one end of a column 2. Thus, in this position of the sampling valve 6, the carrier gas alone is conducted into the column 2 to remove any vestige of the fluid to be analyzed from the column 2 and prepare it for the next analysis operation.

Concurrently, the sample valve loop 20 is reconnected by the internal conduit 6G and 6H to the ports 6F and 6B of the sampling valve 6. However, since the wash solvent is now present in conduit 24, the third position of the sampling valve 6 is effective to allow the solvent wash to clean the port 6F, the internal conduit 6G, the port 6C, the sample loop 20, the port 6D, the internal conduit 6H and the port 6B. Accordingly, the deposits in the sample loop 20 and the aforesaid ports and conduits are removed by the wash solvent to maintain an unclogged state of the valves and conduit while the fluid to be analyzed is exposed to the interior of the oven 8 for only a limited period of time out of each analysis cycle. Thus, the possibility of extensive deposits in the oven enclosed elements from the fluid to be analyzed is further greatly decreased by the decrease in the exposure of the fluid to be analyzed to the oven heat. The further operation of the system of the present invention involves a fourth operation of the timer 38 to restore the valves 6, 26 and 32 to their initial state as shown in FIG. 1. It should be noted that the second valve 32 provides a safety factor by allowing any leakage of the wash solvent during the time that the solvent wash is not being employed to flow out of the port 32B to the drain. Since the drain is a low pressure area as compared with the sample fluid conduit 24, the wash solvent is blocked from entering the sample line and the chromatographic column 2 during the time that the sample fluid is being introduced into the sample loop 20. This solvent drain prevents any damage to the column 2 by the solvent.

Accordingly, it may be seen that there has been provided, in accordance with the present invention, an improved chromatographic analysis system having a solvent wash for sample fluid conduting elements while minimizing deposits from the sample in the sample contacting system elements.

The embodiments of the invention in which an exclusive property or privilege is claimed are defined as follows:

1. A chromatographic analyzer system comprising
    a fluid flow detector having an input and an output,
    a chromatographic column having an input and having an output connected to said input of said detector,
    a sampling valve having a first input, a second input and a third input and a first output, a second output and a third output, said first output of said sampling valve being connected to said input of said column,
    a fluid sample storage loop connected between said first input of said sampling valve and said second output of said sampling valve,
    a first fluid switching valve having two inputs and one output,
    a second fluid switching valve having two inputs and one output,
    a fluid conduit arranged at one end for connection to a source of a sample fluid to be analyzed and connected at the other end to a first input of said first fluid switching valve,
    a second fluid conduit connecting said output of said first switching to said second input of said sampling valve,
    a third fluid conduit arranged at one end for connection to a continuous flow source of a wash solvent and connected at the other end to a second input of said second switching valve,
    a fourth fluid conduit connecting said output of said second switching valve to a second input of said first switching valve,
    a fifth fluid conduit arranged at one end for connection to a carrier gas source and connected at the other end to said third input of said sampling valve,
    said first and second valves being arranged to selectively connect their output to said first and second inputs in a first and second valve position respectively, and said sampling valve being arranged to selectively connect said second input to said first input and said second output to said third output in one mode of operation and said first input to said third input and said second output to said first output in a second mode of operation, and
    timer means for operating said sampling valve and said first and second switching valves in a desired sequence, said sequence selectively and concurrently operating said first and second switching valves between said first and second positions while said sampling valve is in said one mode of operation.

2. A chromatographic analyzer system as set forth in claim 1 wherein said third output of said sampling valve and said first output of said second switching valve are connected to a fluid drain.

3. A chromatographic analyzer system as set forth in claim 1 wherein said sampling valve is arranged to connect remaining ones of said input and output ports in said first and second modes of operation.

4. A chromatographic analyzer as set forth in claim 1 and including an oven encompassing said detector, said column and said sampling valve.

5. A method of operating a chromatographic analyzer system comprising the steps of introducing by a sampling valve a fluid to be analyzed into a sample loop, connecting a first switching valve to a sample source, connecting a second switching valve to a wash solvent source, connecting said sample loop with a trapped fluid sample between a source of a carrier fluid and a chromatographic column to drive said fluid sample into said chromatographic column, detecting the fluid constituents of said fluid sample leaving said chromatographic column and subsequently switching said first and second switching valves to sequentially connect said sample loop and said sample valve directly to the source continuous flow of a wash solvent to clean said sample loop and said sample valve while maintaining a connection of said column to said source of a carrier fluid.

6. The method as set forth in claim 5 and including the further step of reconnecting said sample loop to said source of fluid to be analyzed following said washing of said sample loop by said wash solvent.

7. A method as set forth in claim 5 and including the further step of reconnecting the source of carrier fluid directly to said chromatographic column to remove said fluid sample from said chromatographic column.

8. The method as set forth in claim 7 and including the further step of reconnecting said sample loop to said source of fluid to be analyzed following said washing of said sample loop by said wash solvent.

* * * * *